US012636042B2

(12) United States Patent
Zhang et al.

(10) Patent No.: US 12,636,042 B2
(45) Date of Patent: May 26, 2026

(54) AUGMENTED REALITY (AR)-ASSISTED ENHANCED FRACTURE REDUCTION FIXATOR

(71) Applicant: The Fourth Medical Center of the Chinese People's Liberation Army General Hospital, Beijing (CN)

(72) Inventors: Licheng Zhang, Beijing (CN); Peifu Tang, Beijing (CN); Chi Ma, Beijing (CN); Xiang Cui, Beijing (CN); Houchen Lv, Beijing (CN); Junsong Wang, Beijing (CN); Jiaxu Wang, Beijing (CN)

(73) Assignee: The Fourth Medical Center of the Chinese People's Liberation Army General Hospital, Beijing (CN)

( * ) Notice: Subject to any disclaimer, the term of this patent is extended or adjusted under 35 U.S.C. 154(b) by 0 days.

(21) Appl. No.: 18/963,672

(22) Filed: Nov. 28, 2024

(65) Prior Publication Data

US 2025/0090200 A1 Mar. 20, 2025

(30) Foreign Application Priority Data

Aug. 26, 2024 (CN) .......................... 202411177420.7

(51) Int. Cl.
*A61B 17/64* (2006.01)
*A61B 17/00* (2006.01)
*A61B 90/00* (2016.01)

(52) U.S. Cl.
CPC .................... *A61B 17/6441* (2013.01); *A61B 2017/00991* (2013.01); *A61B 2090/365* (2016.02)

(58) Field of Classification Search
CPC . A61B 17/66; A61B 17/6416; A61B 17/6425; A61B 17/6458; A61B 17/6475;
(Continued)

(56) References Cited

U.S. PATENT DOCUMENTS 2,238,870 A * 4/1941 Haynes .................. A61B 17/66
403/56
4,621,627 A * 11/1986 DeBastiani ............ A61B 17/66
606/57
(Continued)

FOREIGN PATENT DOCUMENTS

CN 209404910 U * 9/2019
CN 114305630 A * 4/2022
(Continued)

*Primary Examiner* — Jacqueline T Johanas

(57) ABSTRACT

An augmented reality (AR)-assisted enhanced fracture reduction fixator includes a bidirectional telescopic rod and two connecting columns, a ball groove is provided in a middle part of each of the two connecting columns, a ball is rotatably connected to an inner wall of each of the two ball grooves, and the two balls are fixedly connected to a telescopic end of the bidirectional telescopic rod. A rectangular slider is slid to a suitable needle insertion position and angle, and a bone nail is inserted into proximal and distal ends of a fracture. Then, the rectangular slider is fixed by screwing. Based on different fracture sites of a patient, two fixing frame bodies need to adapt to the fracture sites of the patient, that is, an angle between the two fixing frame bodies will change. The ball rotates in the corresponding ball groove.

10 Claims, 12 Drawing Sheets

(58) Field of Classification Search
CPC ...... A61B 17/6466; A61B 2017/00991; A61B
17/6441; A61B 17/645; A61B 17/62
See application file for complete search history.

(56) References Cited

U.S. PATENT DOCUMENTS

| | | | | |
|---|---|---|---|---|
| 4,988,349 | A * | 1/1991 | Pennig | A61B 17/66 |
| | | | | 606/57 |
| 5,769,851 | A * | 6/1998 | Veith | A61B 17/66 |
| | | | | 606/57 |
| 5,788,695 | A * | 8/1998 | Richardson | A61B 17/6458 |
| | | | | 606/57 |
| 5,951,556 | A * | 9/1999 | Faccioli | A61B 17/6458 |
| | | | | 606/65 |
| 6,203,548 | B1 * | 3/2001 | Helland | A61B 17/66 |
| | | | | 606/53 |
| 6,245,071 | B1 * | 6/2001 | Pierson | A61B 17/66 |
| | | | | 606/57 |
| 6,716,212 | B1 * | 4/2004 | Pickens | A61B 17/864 |
| | | | | 606/54 |
| 11,166,750 | B1 * | 11/2021 | Wurapa | A61B 17/6416 |
| 12,318,118 | B1 * | 6/2025 | Işin | A61B 17/6416 |
| 2006/0229604 | A1 * | 10/2006 | Olsen | A61B 17/6425 |
| | | | | 606/54 |
| 2011/0093081 | A1 | 4/2011 | Chana et al. | |
| 2016/0022315 | A1 * | 1/2016 | Soffiatti | A61B 17/6425 |
| | | | | 606/54 |
| 2018/0161067 | A1 * | 6/2018 | Dayton | A61B 17/151 |
| 2018/0271507 | A1 * | 9/2018 | Gasser | A61B 17/683 |
| 2019/0365444 | A1 * | 12/2019 | Federspiel | A61B 17/66 |
| 2020/0000492 | A1 * | 1/2020 | Samchukov | A61B 17/66 |
| 2020/0054360 | A1 * | 2/2020 | Wigginton | A61B 17/66 |
| 2021/0137562 | A1 * | 5/2021 | Mislav | A61B 17/6425 |
| 2021/0196325 | A1 * | 7/2021 | Lavi | A61B 17/66 |
| 2021/0330357 | A1 * | 10/2021 | Lavoritano | A61B 17/62 |
| 2021/0393294 | A1 * | 12/2021 | Rodemund | A61B 17/6466 |
| 2022/0266046 | A1 | 8/2022 | Giles et al. | |
| 2022/0280195 | A1 * | 9/2022 | Struik | A61B 17/66 |
| 2022/0354553 | A1 | 11/2022 | Kamath | |
| 2024/0307094 | A1 * | 9/2024 | Yoo | A61B 17/6441 |
| 2025/0090200 | A1 * | 3/2025 | Zhang | A61B 17/66 |
| 2025/0090201 | A1 * | 3/2025 | Isin | A61B 17/6416 |

FOREIGN PATENT DOCUMENTS

| | | | | |
|---|---|---|---|---|
| CN | 119157616 A | * | 12/2024 | ........ A61B 17/6466 |
| WO | WO-9516402 A1 | * | 6/1995 | ........ A61B 17/6491 |
| WO | WO-2021191046 A1 | * | 9/2021 | ............ A61B 17/66 |

* cited by examiner

AUGMENTED REALITY (AR)-ASSISTED ENHANCED FRACTURE REDUCTION FIXATOR

CROSS-REFERENCE TO RELATED APPLICATIONS

This application claims priority to Chinese Patent Application No. 202411177420.7 with a filing date of Aug. 26, 2024. The content of the aforementioned application, including any intervening amendments thereto, is incorporated herein by reference.

TECHNICAL FIELD

The present disclosure relates to the field of medical devices, and more specifically, to an augmented reality (AR)-assisted enhanced fracture reduction fixator.

BACKGROUND

An AR-assisted external fracture reduction fixator integrates an AR technology with a traditional external fixator system to provide a doctor with intuitive and accurate surgical assistance. The AR technology can display an internal structure, a fracture type, and a displacement of a fracture site in real time during an operation, helping the doctor to more accurately judge a fracture condition and perform a precise reduction operation. The external fracture reduction fixator supports and stabilizes the fracture site through an external structure to promote healing and recovery of a fracture.

An existing external fracture reduction fixator usually uses a slider to drive a bone nail to slide on the fixator. When the slider slides to a fracture site that needs to be fixed, the slider is fixed by a screw. However, the screw is prone to loosening during use, resulting in instability of the external fixator and a displacement of a fracture end, which in turn affects a healing process and effect of the fracture. For a current fixator, an angle needs to be adjusted based on different fracture sites of different patients, but it is inconvenient to adjust the angle of the current fixator. As a result, it is difficult for the fixator to adapt to a change in bone morphology in the healing process of the fracture, and a treatment effect is poor.

SUMMARY

In view of the fact that a screw in the prior art is prone to loosening during use, resulting in instability of an external fixator, and easily causing a fracture end to shift, thereby affecting a healing process and effect of a fracture. For a current fixator, an angle needs to be adjusted based on different fracture sites of different patients, but it is inconvenient to adjust the angle of the current fixator. As a result, it is difficult for the fixator to adapt to a change in bone morphology in the healing process of the fracture, and a treatment effect is poor. An objective of the present disclosure is to provide an AR-assisted enhanced fracture reduction fixator.

To solve the above problems, the present disclosure adopts the following technical solutions.

An AR-assisted enhanced fracture reduction fixator includes a bidirectional telescopic rod and two connecting columns, where a ball groove is provided in a middle part of each of the two connecting columns, a ball is rotatably connected to an inner wall of each of the two ball grooves, the two balls are fixedly connected to a telescopic end of the bidirectional telescopic rod, the two connecting columns each are fixedly connected to a fixing frame body on one side away from the bidirectional telescopic rod, a chute is provided on the fixing frame body, two rectangular sliders are slidably connected to an inner wall of the chute, the two rectangular sliders each are threadedly connected to a screw, an upper end of the screw is provided with a bone nail, and the bone nail passes through the rectangular slider, the connecting column is provided with a connecting rod for limiting the ball, and the fixing frame body is provided with a rectangular sleeve for locking the screw.

Optionally, the two connecting rods are separately fixedly connected to an outer surface of the ball, a rectangular groove is provided in the middle part of the connecting column, a push rod is slidably connected to the connecting rod, a circular plate is fixedly connected to an outer surface of the push rod, a first spring is fixedly connected between an outer surface of the connecting rod and the circular plate, the first spring is sleeved on an outer side of the push rod, a rubber sheet is fixedly connected to a bottom end of the push rod, a first screw rod is threadedly connected to the connecting column, the first screw rod threadedly passes through an upper end of the connecting column, a twist block is fixedly connected to a top end of the first screw rod, and an arc plate is fixedly connected to a bottom end of the first screw rod.

Optionally, the rectangular sleeve is fixedly connected to a right-side fixing frame body, an inner wall of the rectangular sleeve is rotatably connected to a wire drum, an outer surface of the wire drum is wound with a wire, both the screw and the twist block are provided with a wire hole, the wire passes through the wire hole, a front end of the wire drum is fixedly connected to a rotating shaft, the rotating shaft rotatably passes through a front end of the rectangular sleeve, a front end of the rotating shaft is fixedly connected to a knob, and a left-side fixing frame body is provided with a round rod for tightening the wire.

Optionally, a fixing column is fixedly connected to the front end of the rectangular sleeve, a connecting plate is slidably connected to an outer surface of the fixing column, a second spring is fixedly connected between one side of the connecting plate and the rectangular sleeve, the second spring is sleeved on an outer side of the fixing column, a latch is fixedly connected to one side of the connecting plate, a disc is fixedly connected to an outer surface of the rotating shaft, a plurality of slots that cooperate with the latch are provided on the disc, a handle is fixedly connected to the other side of the connecting plate, and a limit plate is fixedly connected to a front end of the fixing column.

Optionally, the round rod is fixedly connected to a front end of the left-side fixing frame body, the front end of the fixing frame body is fixedly connected to a first gear, a placement groove is provided on the round rod, and the wire is wound in the placement groove.

Optionally, the front end of the left-side fixing frame body is fixedly connected with a second screw rod, a front end of the second screw rod is fixedly connected with a first rotating block, the second screw rod is threadedly connected to a threaded sleeve, one side of the threaded sleeve is fixedly connected to a hollow shell, a front end of the hollow shell is provided with a tooth groove that cooperates with the first gear, the front end of the left-side fixing frame body is fixedly connected to a limit rod, an outer surface of the limit rod is slidably connected to a rectangular block, one side of the rectangular block is fixedly connected to the threaded sleeve, and a front end of the limit rod is fixedly connected to a limit block.

Optionally, a cutting plate is fixedly connected to an inner bottom wall of the rectangular sleeve, a fixing block is fixedly connected to a top end of the cutting plate in a left-right symmetrical manner, a knife housing is rotatably connected between two fixing blocks, a cutting knife is fixedly connected to a lower end of the knife housing, a pull rod is fixedly connected to a front end of the knife housing, an L-shaped groove cooperating with the pull rod is provided on the rectangular sleeve, and a rubber block is fixedly connected to an inner wall of the L-shaped groove in the left-right symmetrical manner.

Optionally, a sliding groove is provided in a middle part of each of the two fixing frame bodies, an inner wall of the sliding groove is slidably connected to a connecting frame, one side of the connecting frame is fixedly connected to a limiting block, the wire passes through the limiting block, a front end of the limit block is fixedly connected to a rack plate, the front end of the fixing frame body is fixedly connected to a rectangular shell, an inner wall of the rectangular shell is rotatably connected to a connection rod, the connection rod rotatably passes through an upper end of the rectangular shell, a top end of the connection rod is fixedly connected to a rotating block, an outer surface of the connecting rod is fixedly connected to a second gear, and the second gear and the rack plate are meshed with each other.

Optionally, a fixing plate is fixedly connected to a top end of the rectangular shell in the left-right symmetrical manner, a bidirectional threaded rod rotatably passes through a right-side fixing plate, a left end of the bidirectional threaded rod is rotatably connected to a left-side fixing plate, a right end of the bidirectional threaded rod is fixedly connected to a second rotating block, a clamping plate is threadedly connected to the bidirectional threaded rod in the left-right symmetrical manner, an inner side of each of two clamping plates is fixedly connected to a friction pad, a limiting rod is fixedly connected between the two fixing plates, and the limiting rod slidably passes through two clamping plates.

Optionally, a fixing rod is fixedly connected to the inner wall of the rectangular sleeve in an up-down symmetrical manner, an outer surface of each of two fixing rods is rotatably connected to a guide wheel, and an outer surface of the guide wheel is fixedly connected with a rubber pad.

Compared with the prior art, the technical solutions provided by the present disclosure have at least the following beneficial effects:

In the above solutions, the ball is provided. When the fixing frame body needs to adapt to different fracture states of different patients, the rectangular slider is slid to a suitable needle insertion position and angle, and the bone nail is inserted into proximal and distal ends of a fracture. Then, the rectangular slider is fixed by screwing. Based on different fracture sites of the patients, the two fixing frame bodies need to adapt to the fracture sites of the patients, that is, an angle between the two fixing frame bodies will change. The ball rotates in the corresponding ball groove. Since the ball is spherical, the ball rotates universally in the ball groove, and a length of the bidirectional telescopic rod changes accordingly, which is convenient for adapting to the different fracture states of the different patients. Then, the twist block is screwed downward, and the twist block drives the first screw rod to rotate on the connecting column. Under the action of threads of the first screw rod, the arc plate can be driven to move downward on the connecting rod. When the arc plate contacts the push rod, the arc plate pushes the push rod and the circular plate to move downward, the first spring is stretched, and the push rod drives the rubber sheet to move, such that the rubber sheet contacts the inner wall of the rectangular groove, and the ball can be limited by friction force of the rubber sheet.

The wire is disposed. When the screw and the twist block need to be prevented from loosening, the restriction on the rotating shaft is first released, and the knob is turned. The knob drives the rotating shaft to rotate, and the rotating shaft drives the wire drum to rotate to release the wire. After the release is completed, the handle is loosened, the second spring rebounds, and the connecting plate drives the latch to be inserted into the slot on the disc to restrict the wire drum. Subsequently, the released wire passes through the wire hole. Subsequently, a tail end of the wire is wound into the placement groove on the round rod, and the wire is inserted to a tight state. Subsequently, the first rotating block is turned, and the first rotating block drives the second screw rod to rotate. Under the action of threads of the second screw thread, the threaded sleeve moves, and the threaded sleeve drives the limit plate to slide on the limit rod. The limit rod restricts the threaded sleeve, and the threaded sleeve also drives the hollow shell to move when it moves. When the hollow shell moves to be in contact with the front end of the fixing frame body, the hollow shell can squeeze and fix the wire, and the first gear on the round rod is inserted into the tooth groove to fix the round rod to prevent the screw and the twist block from loosening.

The cutting knife is provided. When the device is used and the wire needs to be cut, the pull rod is pulled and pressed downward, and the pull rod drives the knife housing and the cutting knife to move downward. When the cutting knife contacts the cutting plate, the wire can be cut, which is convenient for fixing the screw and the twist block next time. After the cutting is completed, the pull rod is pulled upward, and the pull rod drives the knife housing and the cutting knife to move upward. When the pull rod moves to an uppermost end and contacts the rubber block, the pull rod can squeeze the rubber block to compress the rubber block. When the pull rod completely passes through the rubber block, the rubber block rebounds to fix the pull rod to prevent the pull rod from moving.

The connecting frame is provided. When it is necessary to adjust a length of the fixing frame body, the restriction on the connecting rod is first released, the rotating block is turned, the rotating block drives the connecting rod to rotate, the connecting rod drives the second gear to rotate, the second gear drives the rack plate, such that the rack plate drives the connecting frame to slide outward in the sliding groove to adjust the length of the fixing frame body. When the fixing frame body is adjusted to a suitable length, the second rotating block is turned, and the second rotating block drives the bidirectional threaded rod to rotate. The bidirectional threaded rod drives the two clamping plates to approach each other to clamp and fix the connecting. Friction force of the clamping plate on the connecting rod can be increased by the friction pad.

BRIEF DESCRIPTION OF THE DRAWINGS

The accompanying drawings, which are incorporated herein and constitute a part of the specification, illustrate embodiments of the present disclosure and, together with the specification, are further used to explain the principles of the present disclosure and to enable those skilled in the relevant art to implement and use the present disclosure.

REFERENCE NUMERALS

Figure 1:
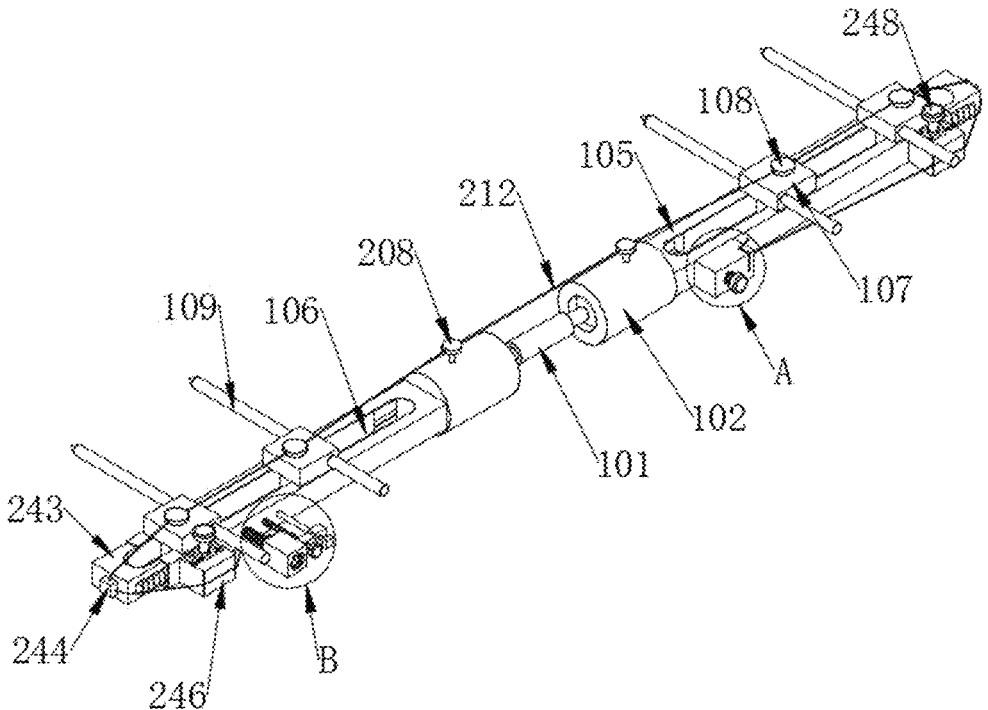
FIG. 1 is a schematic diagram of a three-dimensional structure of the present disclosure.
Figure 2:
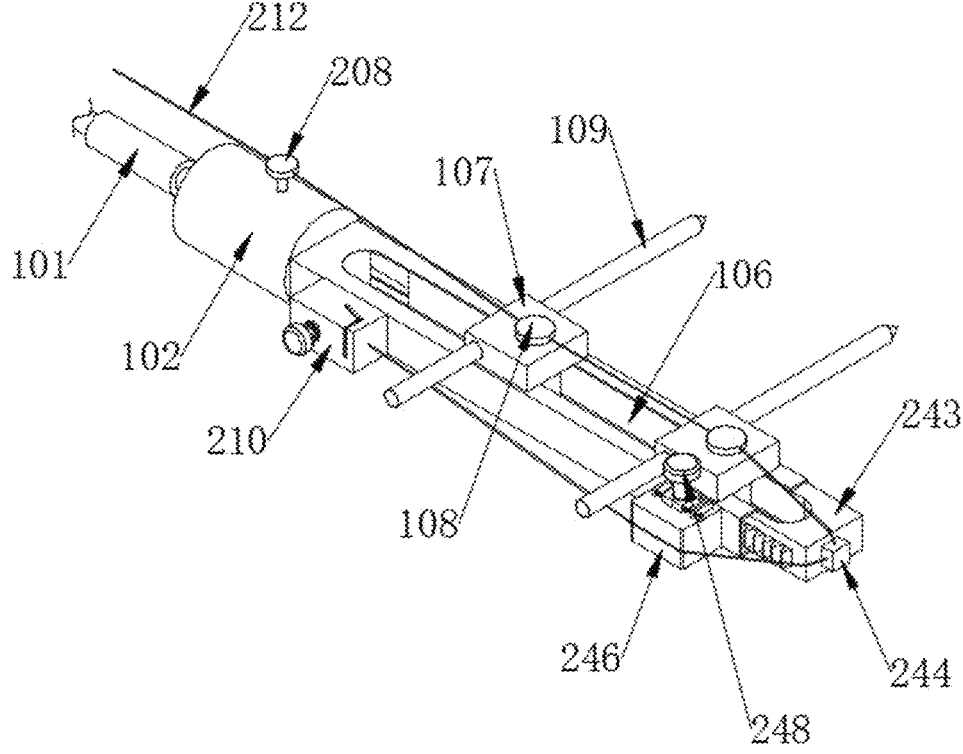
FIG. 2 is a schematic structural diagram of a connecting column and a fixing frame body according to the present disclosure.

101: bidirectional telescopic rod; 102: connecting column; 103: ball groove; 104: ball; 105: fixing frame body; 106: chute; 107: rectangular slider; 108: screw; 109: bone nail; 201: connecting rod; 202: rectangular groove; 203: push rod; 204: round plate; 205: first spring; 206: rubber sheet; 207: first screw rod; 208: twist block; 209: arc plate; 210: rectangular sleeve; 211: wire drum; 212: wire; 213: wire hole; 214: rotating shaft; 215: knob; 216: fixing column; 217: connecting plate; 218: second spring; 219: latch; 220: disc; 221: slot; 222: handle; 223: limit plate; 224: round rod; 225: first gear, 226: placement groove; 227: second screw rod; 228: first rotating block; 229: threaded sleeve; 230: hollow shell; 231: tooth groove; 232: limit rod; 233: rectangular block; 234: limit block; 235: cutting plate; 236: fixing block; 237: knife housing; 238: cutting knife; 239: pull rod; 240: L-shaped groove; 241: rubber block; 242: sliding groove; 243: connecting frame; 244: limiting block; 245: rack plate; 246: rectangular shell; 247: connection rod; 248: rotating block; 249: second gear, 250: fixing plate; 251: bidirectional threaded rod; 252: second rotating block; 253: clamping plate; 254: friction pad; 255: limiting rod; 256: fixing rod; 257: guide wheel.

As shown in the figures, in order to clearly implement the structure in the embodiments of the present disclosure, specific structures and devices are marked in the figures, but this is only for illustrative purposes and is not intended to limit the present disclosure to the specific structures, devices, and environments. According to specific needs, those of ordinary skill in the art can adjust or modify these devices and environments.

DESCRIPTION OF THE EMBODIMENTS

The following is a detailed description of an AR-assisted enhanced fracture reduction fixator provided by the present disclosure in conjunction with the accompanying drawings and specific embodiments. In addition, it is explained herein that in order to make the embodiments more detailed, the following embodiments are the best and preferred embodiments, and those skilled in the art may also adopt other alternatives to implement some known technologies; and the accompanying drawings are only for a more specific description of the embodiments, and are not intended to specifically limit the present disclosure.

It should be noted that the terms "one embodiment", "an embodiment", "an exemplary embodiment", "some embodiments", and the like in the specification indicate that the embodiment/embodiments described may include specific features, structures, or characteristics, but not every embodiment may include the specific features, structures, or characteristics. In addition, when a specific feature, structure, or characteristic is described in conjunction with an embodiment, it should be within the knowledge of a person skilled in the art to implement such a feature, structure, or characteristic in conjunction with other embodiments (whether or not explicitly described).

In general, a term can be understood, at least in part, from its use in context. For example, depending on the context at least in part, the term "at least one" as used herein can be used to describe any feature, structure, or characteristic in a singular sense, or can be used to describe a combination of features, structures, or characteristics in a plural sense. Additionally, the term "based on" can be understood as not necessarily intended to convey a set of exclusive factors, but can instead, depending on the context at least in part, allow for the presence of other factors that are not necessarily explicitly described.

It will be understood that the meanings of "on", "over", and "above" in the present disclosure should be interpreted in a broadest sense, such that "on" not only means "directly on" something, but also includes the meaning of being "on" something with intervening features or layers therebetween, and "over" or "above" not only means "on" or "above" something, but also includes the meaning of being "on" or "above" something with no intervening features or layers therebetween.

Additionally, spatially related terms such as "under," "beneath," "lower," "above," "upper," and the like may be used herein to conveniently describe a relationship between one element or feature and another element or feature, as shown in the accompanying drawings. The spatially related terms are intended to encompass different orientations of using or operating the device in addition to the orientation depicted in the accompanying drawings. The device may be oriented in other ways, and the spatially related descriptors used herein may be similarly interpreted accordingly.

As shown in FIG. 1 to FIG. 12, an embodiment of the present disclosure provides an AR-assisted enhanced fracture reduction fixator, including a bidirectional telescopic rod 101 and two connecting columns 102. A ball groove 103 is provided in a middle part of each of the two connecting columns 102, a ball 104 is rotatably connected to an inner wall of each of the two ball grooves 103, and the two balls 104 are fixedly connected to a telescopic end of the bidirectional telescopic rod 101. The two connecting columns 102 each are fixedly connected to a fixing frame body 105 on one side away from the bidirectional telescopic rod 101. A chute 106 is provided on the fixing frame body 105, and two rectangular sliders 107 are slidably connected to an inner wall of the chute 106. The two rectangular sliders 107 are both threadedly connected to a screw 108, an upper end of the screw 108 is provided with a bone nail 109, and the bone nail 109 penetrates the rectangular slider 107. The When the device is needed, the staff can use an AR technology to display an internal structure of a fracture site of a patient in real time during an operation, and determine a specific position of the bone nail 109 through the AR technology. After the determination is completed, the rectangular slider 107 is slid to a suitable needle insertion position and angle, the bone nail 109 is inserted into proximal and distal ends of a fracture, and then the screw 108 is turned to fix the rectangular slider 107. Based on different fracture sites of the patient, the two fixing frame bodies 105 need to adapt to the fracture sites of the patient, that is, an angle between the two fixing frame bodies 105 will change, and the ball 104 will rotate in the corresponding ball groove 103. Since the ball 104 is spherical, the ball 104 rotates universally in the ball groove 103, and a length of the bidirectional telescopic rod 101 changes accordingly, which is convenient for adapting to different fracture states of different patients.

Figure 3:
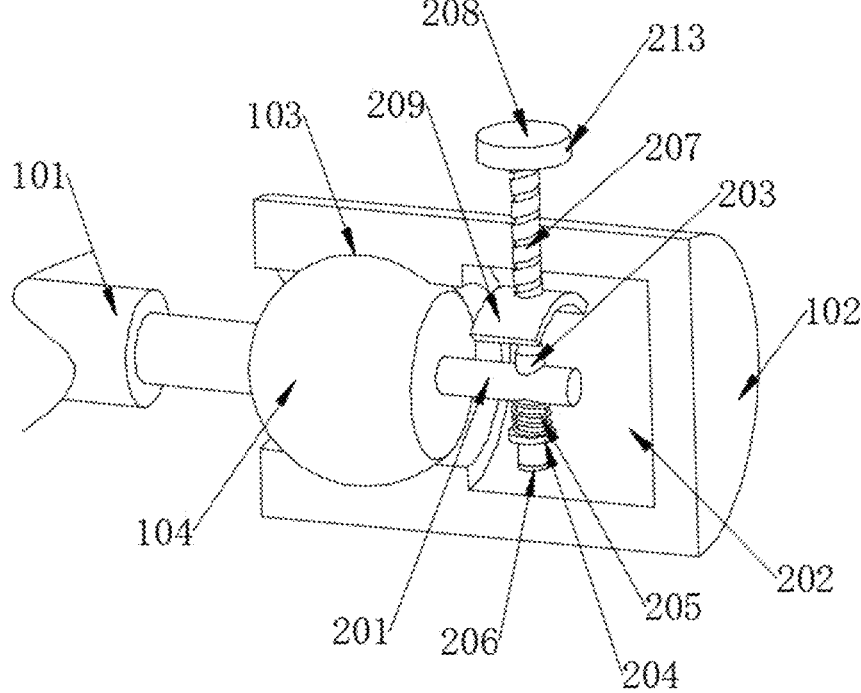
FIG. 3 is a schematic diagram of a front cross-sectional structure of a connecting column according to the present disclosure.

As shown in FIG. 3, the two connecting rods 201 are separately fixedly connected to an outer surface of the ball 104. A rectangular groove 202 is provided in the middle part of the connecting column 102, a push rod 203 is slidably connected to the connecting rod 201, and a circular plate 204 is fixedly connected to an outer surface of the push rod 203. A first spring 205 is fixedly connected between an outer surface of the connecting rod 201 and the circular plate 204, and the first spring 205 is sleeved on an outer side of the push rod 203. A rubber sheet 206 is fixedly connected to a bottom end of the push rod 203. A first screw rod 207 is threadedly connected to the connecting column 102, the first screw rod 207 threadedly passes through an upper end of the connecting column 102. A twist block 208 is fixedly connected to a top end of the first screw rod 207, and an arc plate 209 is fixedly connected to a bottom end of the first screw rod 207.

When it is necessary to limit an angle of the ball 104, the twist block 208 is screwed downward, and the twist block 208 drives the first screw rod 207 to rotate on the connecting column 102. Under the action of threads of the first screw rod 207, the arc plate 209 can be driven to move downward on the connecting rod 201. When the arc plate 209 contacts the push rod 203, the arc plate 209 pushes the push rod 203 and the circular plate 204 to move downward, the first spring 205 is stretched, and the push rod 203 drives the rubber sheet 206 to move, such that the rubber sheet 206 contacts an inner wall of the rectangular groove 202, and the ball 104 is limited by friction force of the rubber sheet 206.

Figure 4:
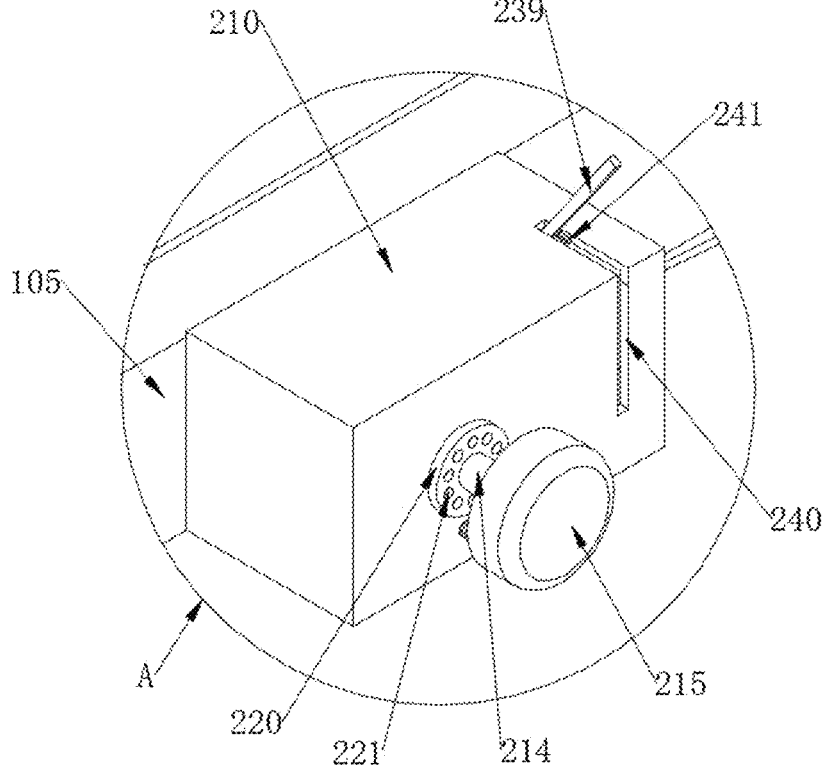
FIG. 4 is an enlarged schematic structural diagram of A in FIG. 1 according to the present disclosure.
Figure 5:
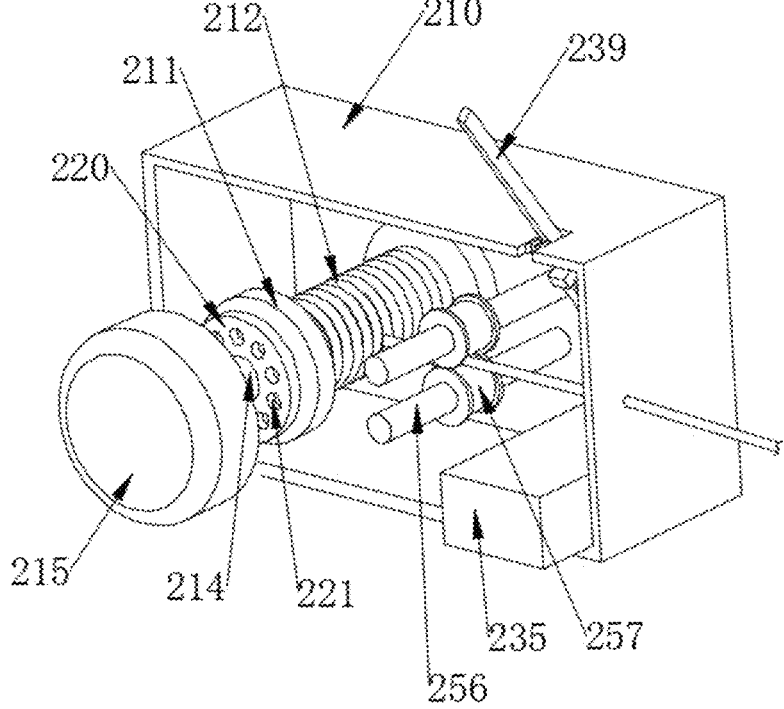
FIG. 5 is a schematic diagram of a front cross-sectional structure of a rectangular sleeve according to the present disclosure.

As shown in FIG. 4 and FIG. 5, the rectangular sleeve 210 is fixedly connected to a right-side fixing frame body 105, an inner wall of the rectangular sleeve 210 is rotatably connected to a wire drum 211, and an outer surface of the wire drum 211 is wound with a wire 212. Both the screw 108 and the twist block 208 are provided with a wire hole 213, and the wire 212 passes through the wire hole 213. A front end of the wire drum 211 is fixedly connected to a rotating shaft 214, the rotating shaft 214 rotatably passes through a front end of the rectangular sleeve 210, and a front end of the rotating shaft 214 is fixedly connected to a knob 215. A left-side fixing frame body 105 is provided with a round rod for tightening the wire 212.

When the screw 108 and the twist block 208 need to be fixed, the knob 215 is turned, and the knob 215 drives the rotating shaft 214 to rotate. The rotating shaft 214 drives the wire drum 211 to rotate, and the wire 212 on the wire drum 211 is released. Subsequently, the released wire 212 passes through the wire holes 213 on the screw 108 and the twist block 208, and the wire 212 is tightened by the round rod to fix the screw 108 and the bone nail 109.

Figure 6:
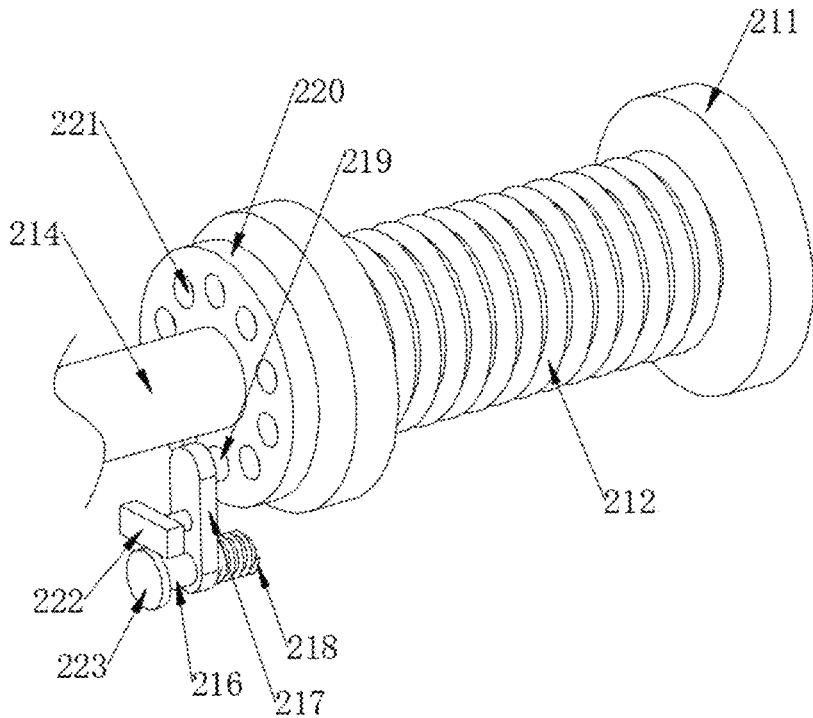
FIG. 6 is a schematic structural diagram of a latch and a slot according to the present disclosure.

As shown in FIG. 6, a fixing column 216 is fixedly connected to the front end of the rectangular sleeve 210, and a connecting plate 217 is slidably connected to an outer surface of the fixing column 216. A second spring 218 is fixedly connected between one side of the connecting plate 217 and the rectangular sleeve 210, and the second spring 218 is sleeved on an outer side of the fixing column 216. A latch 219 is fixedly connected to one side of the connecting plate 217. A disc 220 is fixedly connected to an outer surface of the rotating shaft 214, and a plurality of slots that cooperate with the latch 219 are provided on the disc 220. A handle 222 is fixedly connected to the other side of the connecting plate 217, and a limit plate 223 is fixedly connected to a front end of the fixing column 216.

When it is necessary to limit the wire drum 211, the handle 222 is pulled, and the handle 222 drives the connecting plate 217 to slide on the fixing column 216. The second spring 218 is stretched, and the connecting plate 217 drives the latch 219 to leave the slot 221 on the disk 220. Then, the knob 215 is turned, the knob 215 drives the rotating shaft 214 and the disk 220 to rotate, and the rotating shaft 214 drives the wire drum 211 to rotate to release the wire 212 on the wire drum 211. After the release is completed, the handle 222 is released, the second spring 218 rebounds, and the connecting plate 217 drives the latch 219 to be inserted into the slot 221 on the disk 220 to limit the wire drum 211. The connecting plate 217 can be limited by the limit plate 223 to prevent the handle 222 from driving the connecting plate 217 to slide out of the fixing column 216 when the handle 222 is pulled.

Figure 7:
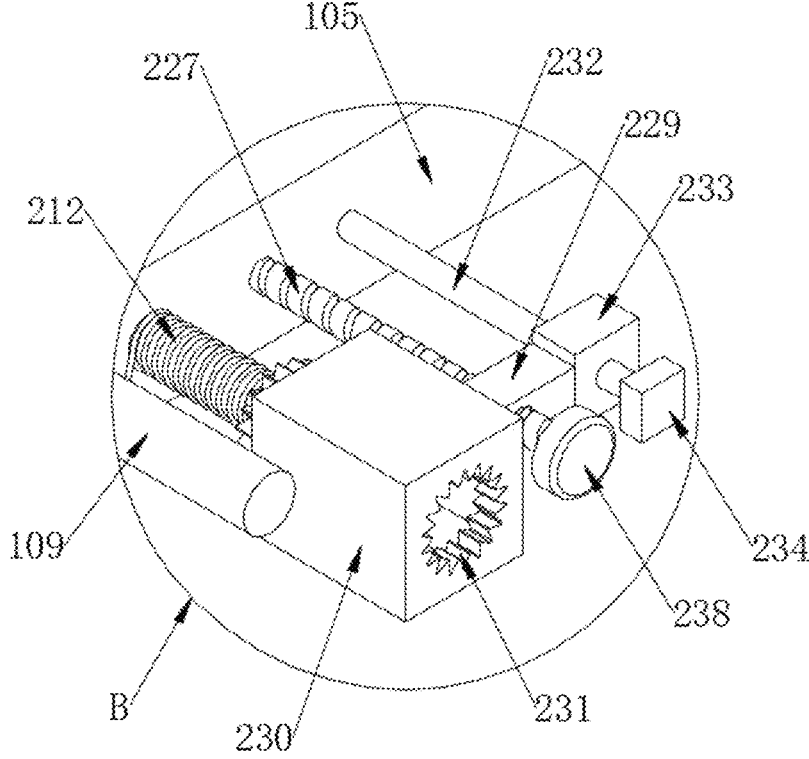
FIG. 7 is an enlarged schematic structural diagram of B in FIG. 1 according to the present disclosure.
Figure 8:
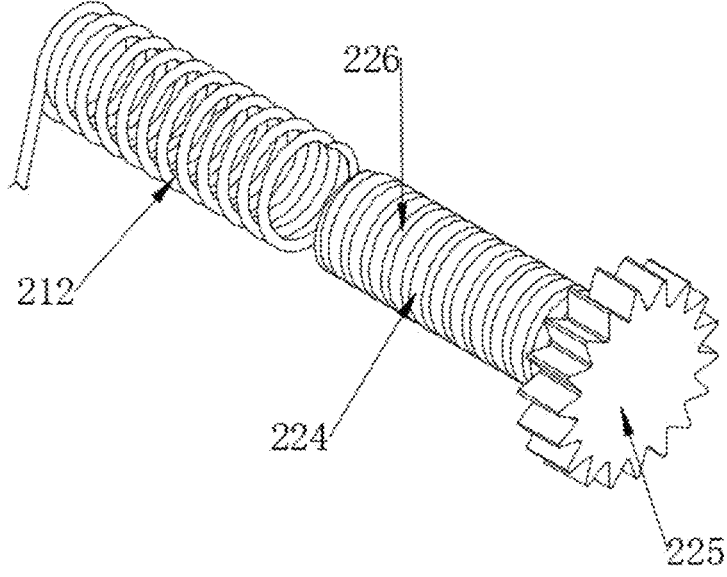
FIG. 8 is a schematic structural diagram of a round rod and a placement groove according to the present disclosure.

As shown in FIG. 7 and FIG. 8, the round rod 224 is fixedly connected to a front end of the left-side fixing frame body 105, and the front end of the fixing frame body 105 is fixedly connected to a first gear 225. A placement groove 226 is provided on the round rod 224, and the wire 212 is wound in the placement groove 226.

When the wire 212 needs to be tightened, the wire 212 is enabled to pass through the wire holes 213 on the screw 108 and the twist block 208, and a tail end of the wire 212 is wrapped along the placement groove 226 on the round rod 224 to tighten the wire 212, such that the wire 212 is in a tight state to prevent the screw 108 and the twist block 208 from loosening.

Figure 9:
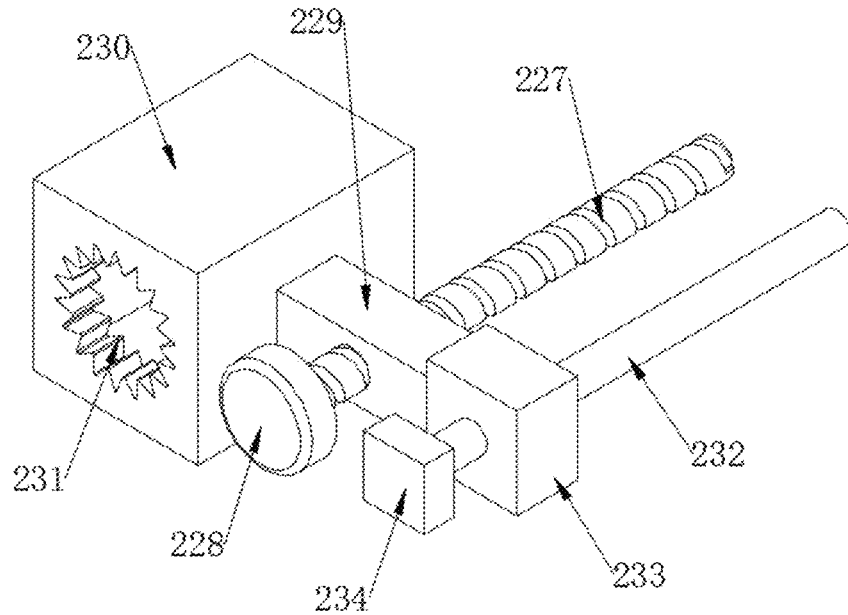
FIG. 9 is a schematic structural diagram of a second screw rod and a hollow shell according to the present disclosure.

As shown in FIG. 7 and FIG. 9, the front end of the left-side fixing frame body 105 is fixedly connected to a second screw rod 227, a front end of the second screw rod 227 is fixedly connected to a first rotating block 228, and the second screw rod 227 is threadedly connected to a threaded sleeve 229. One side of the threaded sleeve 229 is fixedly connected to a hollow shell 230, and a front end of the hollow shell 230 is provided with a tooth groove 231 that cooperates with the first gear 225. The front end of the left-side fixing frame body 105 is fixedly connected to a limit rod 232, an outer surface of the limit rod 232 is slidably connected to a rectangular block 233, and one side of the rectangular block 233 is fixedly connected to the threaded sleeve 229. A front end of the limit rod 232 is fixedly connected to a limit block 234.

When it is necessary to fix the wire 212 in the tight state, the first rotating block 228 is turned, and the first rotating block 228 drives the second screw rod 227 to rotate. Under the action of threads of the second screw rod 227, the first rotating block 228 drives the threaded sleeve 229 to move, and the threaded sleeve 229 drives the limit plate 223 to slide on the limit rod 232 to limit the threaded sleeve 229. When the threaded sleeve 229 moves, it also drives the hollow shell 230 to move. When the hollow shell 230 moves to be in contact with the front end of the fixing frame body 105, the hollow shell 230 can squeeze and fix the wire 212, and the first gear 225 on the round rod 224 is inserted into the tooth groove 231 to fix the round rod 224.

Figure 10:
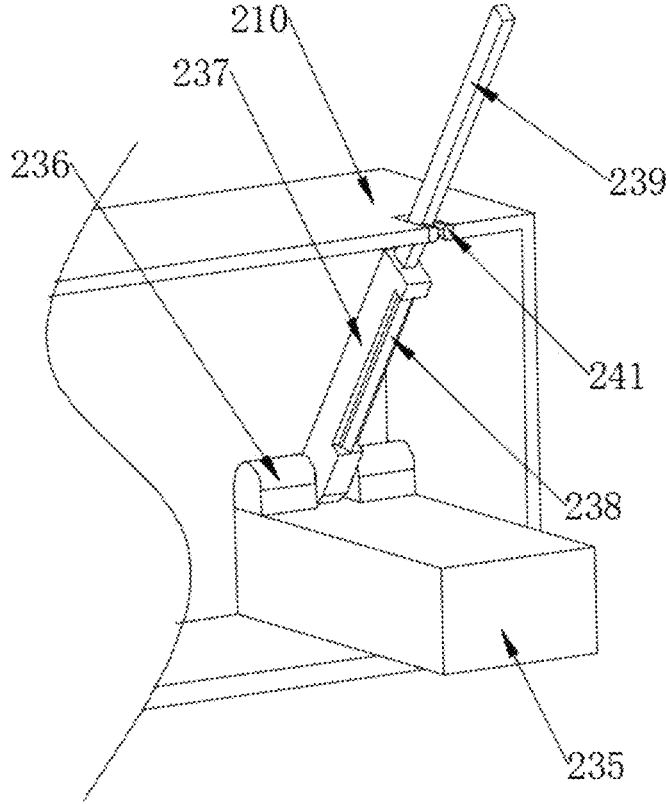
FIG. 10 is a schematic structural diagram of a knife housing and a cutting knife according to the present disclosure.

As shown in FIG. 10, a cutting plate 235 is fixedly connected to an inner bottom wall of the rectangular sleeve 210, a fixing block 236 is fixedly connected to a top end of the cutting plate 235 in a left-right symmetrical manner, and a knife housing 237 is rotatably connected between two fixing blocks 236. A cutting knife 238 is fixedly connected to a lower end of the knife housing 237, and a pull rod 239 is fixedly connected to a front end of the knife housing 237. An L-shaped groove 240 cooperating with the pull rod 239 is provided on the rectangular sleeve 210, and a rubber block 241 is fixedly connected to an inner wall of the L-shaped groove 240 in the left-right symmetrical manner.

When it is necessary to cut the wire 212, the pull rod 239 is pressed downward to move the pull rod 239 in the L-shaped groove 240, and the pull rod 239 drives the knife housing 237 and the cutting knife 238 to move downward. When the cutting knife 238 contacts the cutting plate 235, the wire 212 can be cut, which is convenient for fixing the screw 108 and the twist block 208 next time. After the cutting is completed, the pull rod 239 is pulled upward to drive the knife housing 237 and the cutting knife 238 to move upward. When the pull rod 239 moves to an uppermost end and contacts the rubber block 241, the pull rod 239 can squeeze the rubber block 241 to compress the rubber block 241. When the pull rod 239 completely passes through the rubber block 241, the rubber block 241 rebounds to fix the pull rod 239 to prevent the pull rod 239 from moving.

Figure 11:
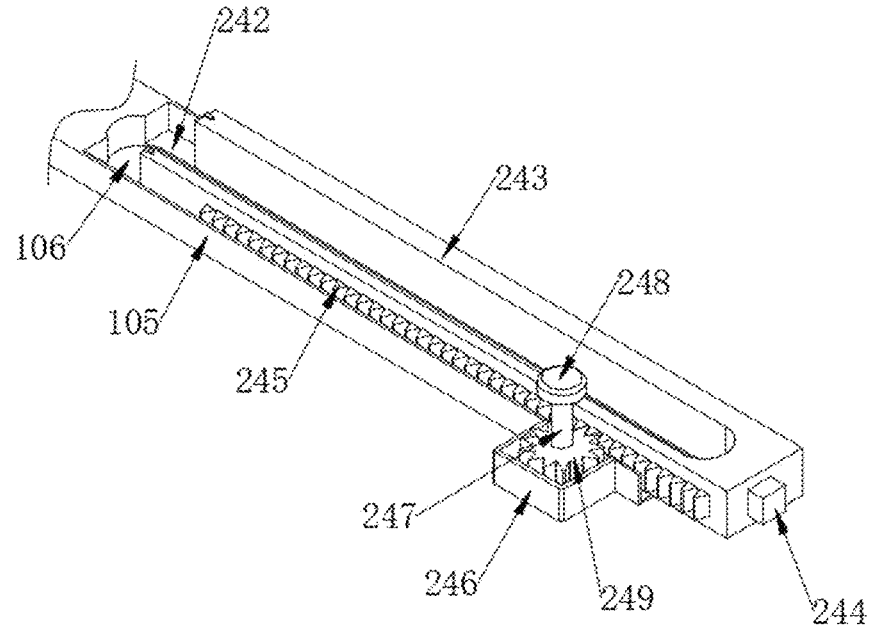
FIG. 11 is a schematic structural diagram of a limit block and a rack plate according to the present disclosure.
Figure 12:
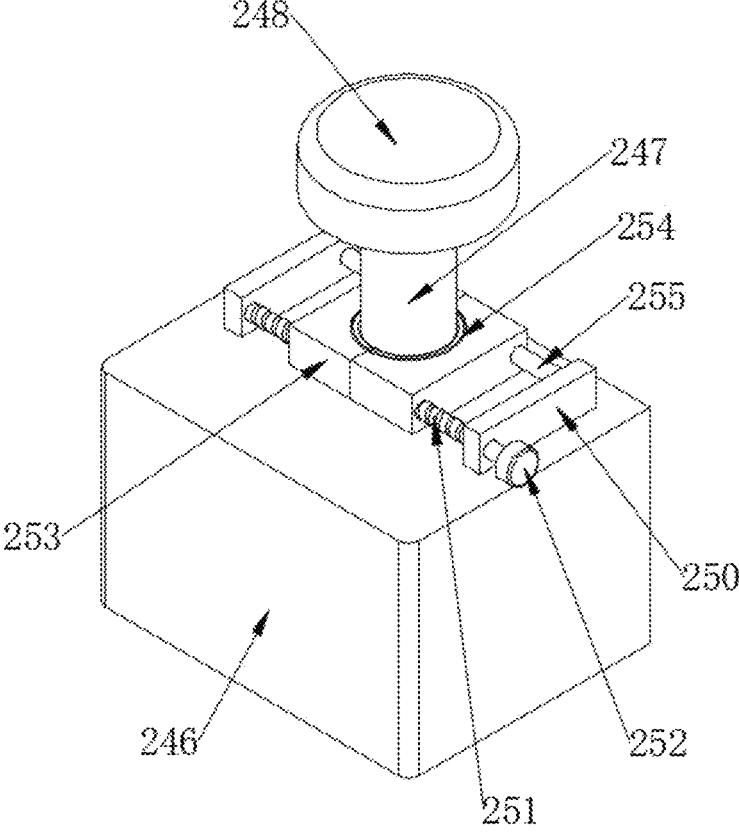
FIG. 12 is a schematic structural diagram of a bidirectional threaded rod and a clamping plate according to the present disclosure.

As shown in FIG. 11, a sliding groove 242 is provided in a middle part of each of the two fixing frame bodies 105, an inner wall of the sliding groove 242 is slidably connected to a connecting frame 243, and one side of the connecting frame 243 is fixedly connected to a limiting block 244. The wire 212 passes through the limiting block 244, and a front end of the limit block 234 is fixedly connected to a rack plate 245. The front end of the fixing frame body 105 is fixedly connected to a rectangular shell 246, an inner wall of the rectangular shell 246 is rotatably connected to a connection rod 247, and the connection rod 247 rotatably passes through an upper end of the rectangular shell 246. A top end of the connection rod 247 is fixedly connected to a rotating block 248, an outer surface of the connection rod 247 is fixedly connected to a second gear 249, and the second gear 249 and the rack plate 245 are meshed with each other.

When it is necessary to adjust a length of the fixing frame body 105, the rotating block 248 is turned, and the rotating block 248 drives the connection rod 247 to rotate. The connection rod 247 drives the second gear 249 to rotate, and the second gear 249 drives the rack plate 245, such that the rack plate 245 drives the connecting frame 243 to slide outward in the sliding groove 242, and the length of the fixing frame body 105 is adjusted. The wire 212 can be limited by the limiting block bidirectional threaded rod 251 rotatably passes through a right-side fixing plate 250. A left end of the bidirectional threaded rod 251 is rotatably connected to a left-side fixing plate 250, and a right end of the bidirectional threaded rod 251 is fixedly connected to a second rotating block 252. A clamping plate 253 is threadedly connected to the bidirectional threaded rod 251 in the left-right symmetrical manner, and an inner side of each of two clamping plates 253 is fixedly connected to a friction pad 254. A limiting rod 255 is fixedly connected between the two fixing plates 250, and the limiting rod 255 slidably passes through the two clamping plates 253.

When it is necessary to limit the connection rod 247, the second rotating block 252 is turned, and the second rotating block 252 drives the bidirectional threaded rod 251 to rotate on the fixing plate 250. Under the action of threads of the bidirectional threaded rod 251, the bidirectional threaded rod 251 drives the two clamping plates 253 to move outward, and the friction pad 254 can be limited by the limiting rod 255. Subsequently, the rotating block 248 is turned, the rotating block 248 drives the connection rod 247 to rotate, the connection rod 247 drives the second gear 249 to rotate, and the second gear 249 drives the rack plate 245, such that the rack plate 245 drives the connecting frame 243 to slide outward in the sliding groove 242 to adjust the length of the fixing frame body 105. After the adjustment is completed, the second rotating block 252 is turned in an opposite direction, and the second rotating block 252 drives the bidirectional threaded rod 251 to rotate. The bidirectional threaded rod 251 drives the two clamping plates 253 to approach each other to clamp and fix the connection rod 247. The friction pad 254 can increase friction force of the clamping plate 253 on the connection rod 247.

As shown in FIG. 5, a fixing rod 256 is fixedly connected to the inner wall of the rectangular sleeve 210 in an up-down symmetrical manner, an outer surface of each of two fixing rods 256 is rotatably connected to a guide wheel 257, and an outer surface of the guide wheel 257 is fixedly connected with a rubber pad.

The fixing rod 256 and the guide wheel 257 are provided. Therefore, when the wire 212 is released, the guide wheel 257 can guide the wire 212, and the rubber pad can protect the wire 212.

A working process provided by the present disclosure is as follows:

When the present disclosure is in use, the staff can use the AR technology to display the internal structure of the fracture site of the patient in real time during the operation, and determine the specific position of the bone nail 109 through the AR technology. After the determination is completed, the rectangular slider 107 is slid to the suitable needle insertion position and angle, the bone nail 109 is into the proximal and distal ends of the fracture, and then the screw 108 is turned to fix the rectangular slider 107.

Based on the different fracture sites of the patient, the two fixing frame bodies 105 need to adapt to the fracture sites of the patient, that is, the angle between the two fixing frame bodies 105 will change, and the ball 104 will rotate in the corresponding ball groove 103. Since the ball 104 is spherical, the ball 104 rotates universally in the ball groove 103. The length of the bidirectional telescopic rod 101 changes accordingly, so as to adapt to the different fracture states of the different patients.

Then, the twist block 208 is turned downward, and the twist block 208 drives the first screw rod 207 to rotate on the connecting column 102. Under the action of the threads of the first screw rod 207, the arc plate 209 can be driven to move downward on the connecting rod 201. When the arc plate 209 contacts the push rod 203, the arc plate 209 pushes the push rod 203 and the circular plate 204 to move downward. The first spring 205 is stretched, and the push rod 203 drives the rubber sheet 206 to move, such that the rubber sheet 206 contacts with the inner wall of the rectangular groove 202, and the ball 104 is limited by the friction force of the rubber sheet 206. The handle 222 is pulled, and the handle 222 drives the connecting plate 217 to slide on the fixing column 216. The second spring 218 is stretched, and the connecting plate 217 drives the latch 219 to leave the slot 221 on the disc 220.

Then the knob 215 is turned, the knob 215 drives the rotating shaft 214 to rotate, the rotating shaft 214 drives the wire drum 211 to rotate, and the wire 212 on the wire drum 211 is released. The two guide wheels 257 guide the wire 212, and the rubber pad on the outer surface of the guide wheel 257 protects the wire 212. After the release is completed, the handle 222 is released, the second spring 218 rebounds, the connecting plate 217 drives the latch 219 to be inserted into the slot 221 on the disc 220, and the wire drum 211 is limited. The connecting plate 217 can be limited by the limiting plate 223 to prevent the handle 222 from driving the connecting plate 217 to slide out of the fixing column 216 when the handle 222 is pulled.

Subsequently, the released wire 212 passes through one side of the left-side rectangular shell 246, passes through the right-side limiting block 244, passes through the wire holes 213 on the screw 108 and the twist block 208, passes through the left-side limiting block 244, and then passes through the left-side rectangular shell 246. On one side of the rectangular shell 246, the tail end of the wire 212 is wound into the placement groove 226 on the round rod 224, and the wire 212 is tightened to keep the wire 212 in the tight state to prevent the screw 108 and the twist block 208 from loosening. Subsequently, the first rotating block 228 is turned, and the first rotating block 228 drives the second screw rod 227 to rotate. Under the action of the threads of the second screw rod 227, the first rotating block 228 drives the threaded sleeve 229 to move, and the threaded sleeve 229 drives the limit plate 223 to slide on the limit rod 232 to limit the threaded sleeve 229. When the threaded sleeve 229 moves, it also drives the hollow shell 230 to move. When the hollow shell 230 moves to be in contact with the front end of the fixing frame body 105, the hollow shell 230 can squeeze and fix the wire 212, and the first gear 225 on the round rod 224 is inserted into the tooth groove 231 to fix the round rod 224. The second rotating block 252 is turned, and the second rotating block 252 drives the bidirectional threaded rod 251 to rotate on the fixing plate 250. Under the action of the threads of the bidirectional threaded rod 251, the bidirectional threaded rod 251 drives the two clamping plates 253 to move outward, and the friction pad 254 can be limited by the limiting rod 255.

Subsequently, the rotating block 248 is turned, the rotating block 248 drives the connection rod 247 to rotate, the connection rod 247 drives the second gear 249 to rotate, and the second gear 249 drives the rack plate 245, such that the rack plate 245 drives the connecting frame 243 to slide outward in the sliding groove 242, and the length of the fixing frame body 105 is adjusted. When the connecting frame 243 is adjusted to the suitable length, the second rotating block 252 is turned in the opposite direction, and the second rotating block 252 drives the bidirectional threaded rod 251 to rotate. The bidirectional threaded rod 251 drives the two clamping plates 253 to approach each other to clamp and fix the connection rod 247. The friction pad 254 can increase the friction force of the clamping plate 253 on the connection rod 247. When the device is used, the pull rod 239 is pressed downward to move the pull rod 239 in the L-shaped groove 240. The pull rod 239 drives the knife housing 237 and the cutting knife 238 to move downward. When the cutting knife 238 contacts the cutting plate 235, the wire 212 can be cut, which is convenient for fixing the screw 108 and the twist block 208 next time. After the cutting is completed, the pull rod 239 is pulled upward. The pull rod 239 drives the knife housing 237 and the cutting knife 238 to move upward. When the pull rod 239 moves to the uppermost end and contacts the rubber block 241, the pull rod 239 can squeeze the rubber block 241 to compress the rubber block 241. When the pull rod 239 completely passes through the rubber block 241, the rubber block 241 rebounds to fix the pull rod 239 to prevent the pull rod 239 from moving.

The present disclosure covers any substitution, modification, equivalent method, and scheme made on the essence and scope of the present disclosure. In order to make the public have a thorough understanding of the present disclosure, specific details are described in detail in the following preferred embodiments of the present disclosure, but those skilled in the art can fully understand the present disclosure without the description of these details. In addition, in order to avoid unnecessary confusion about the essence of the present disclosure, well-known methods, processes, procedures, components, and circuits are not described in detail.

The above are only preferred implementations of the present disclosure. It should be pointed out that those of ordinary skill in the art can also be made several improvements and modifications without departing from the principle of the present disclosure. These improvements and modifications should also be regarded as the scope of protection of the present disclosure.

What is claimed is:

1. An augmented reality (AR)-assisted enhanced fracture reduction fixator, comprising a bidirectional telescopic rod and two connecting columns, wherein a ball groove is provided in a middle part of each of the two connecting columns, a ball is rotatably connected to an inner wall of each of the two ball grooves, the two balls are fixedly connected to a telescopic end of the bidirectional telescopic rod, each of the two connecting columns is fixedly connected to a fixing frame body on one side away from the bidirectional telescopic rod, a chute is provided on each of the two fixing frame bodies, and two rectangular sliders are slidably connected to inner walls of the two chutes, respectively; and each of the rectangular sliders is threadedly connected to a screw, bone nails pass through the rectangular sliders, respectively, each of the two connecting columns is provided with a connecting rod for limiting one of the two balls, and each of the two fixing frame bodies is provided with a rectangular sleeve for locking the screws.

2. The AR-assisted enhanced fracture reduction fixator according to claim 1, wherein the two connecting rods are fixedly connected to outer surfaces of the two balls, respectively, a rectangular groove is provided in the middle part of each of the two connecting columns, each connecting rod is slidably connected to a push rod, a circular plate is fixedly connected to an outer surface of each push rod, a first spring is fixedly connected between an outer surface of each connecting rod and each circular plate, the first spring is sleeved on an outer side of each push rod, a bottom end of each push rod is fixedly connected to a rubber sheet, each of the two connecting columns is threadedly connected to a first screw rod, the first screw rods threadedly pass through upper ends of the two connecting columns, respectively, twist blocks are fixedly connected to top ends of the two first screw rods, respectively, and arc plates are fixedly connected to bottom ends of the two first screw rods, respectively.

3. The AR-assisted enhanced fracture reduction fixator according to claim 2, wherein each rectangular sleeve is fixedly connected to a right-side fixing frame body, an inner wall of each rectangular sleeve is rotatably connected to a wire drum, an outer surface of each wire drum is wound with a wire, each of the screws and the twist blocks is provided with a wire hole, the wires pass through the wire holes, respectively, a front end of each wire drum is fixedly connected to a rotating shaft, the rotating shafts rotatably pass through front ends of the rectangular sleeves, respectively, a front end of each rotating shaft is fixedly connected to a knob, and a left-side fixing frame body is provided with a round rod for tightening the wire.

4. The AR-assisted enhanced fracture reduction fixator according to claim 3, wherein a fixing column is fixedly connected to the front end of each rectangular sleeve, a connecting plate is slidably connected to an outer surface of each fixing column, a second spring is fixedly connected between one side of each connecting plate and each rectangular sleeve, the second spring is sleeved on an outer side of each fixing column, a latch is fixedly connected to one side of each connecting plate, a disc is fixedly connected to an outer surface of each rotating shaft, a plurality of slots that cooperate with the latches are provided on the discs, a handle is fixedly connected to another side of each connecting plate, and a limit plate is fixedly connected to a front end of each fixing column.

5. The AR-assisted enhanced fracture reduction fixator according to claim 4, wherein each round rod is fixedly connected to a front end of the left-side fixing frame body, the front end of the left-side fixing frame body is fixedly connected to a first gear, a placement groove is provided on each round rod, and the wire is wound in each placement groove.

6. The AR-assisted enhanced fracture reduction fixator according to claim 5, wherein the front end of the left-side fixing frame body is fixedly connected to a second screw rod, a front end of the second screw rod is fixedly connected to a first rotating block, the second screw rod is threadedly connected to a threaded sleeve, one side of the threaded sleeve is fixedly connected to a hollow shell, a front end of the hollow shell is provided with a tooth groove that cooperates with the first gear, the front end of the left-side fixing frame body is fixedly connected to a limit rod, an outer surface of the limit rod is slidably connected to a rectangular block, one side of the rectangular block is fixedly connected to the threaded sleeve, and a front end of the limit rod is fixedly connected to a limit block.

7. The AR-assisted enhanced fracture reduction fixator according to claim 6, wherein a cutting plate is fixedly connected to an inner bottom wall of each rectangular sleeve, a top end of each cutting plate is fixedly connected to a fixing block in a left-right symmetrical manner, a knife housing is rotatably connected between the two fixing blocks, a cutting knife is fixedly connected to a lower end of the knife housing, a pull rod is fixedly connected to a front end of the knife housing, an L-shaped groove cooperating with the pull rod is provided on each rectangular sleeve, and a rubber block is fixedly connected to an inner wall of the L-shaped groove in the left-right symmetrical manner.

8. The AR-assisted enhanced fracture reduction fixator according to claim 7, wherein a sliding groove is provided in a middle part of each of the two fixing frame bodies, an inner wall of each sliding groove is slidably connected to a connecting frame, one side of each connecting frame is fixedly connected to a limiting block, the wire passes through the limiting block, a front end of the limit block is fixedly connected to a rack plate, the front end of each of the two fixing frame bodies is fixedly connected to a rectangular shell, an inner wall of each rectangular shell is rotatably connected to a connection rod, each connection rod rotatably passes through an upper end of the rectangular shell, a top end of each connection rod is fixedly connected to a rotating block, an outer surface of each connection rod is fixedly connected to a second gear, and the second gear and the rack plate are meshed with each other.

9. The AR-assisted enhanced fracture reduction fixator according to claim 8, wherein a fixing plate is fixedly connected to a top end of each rectangular shell in the left-right symmetrical manner, a bidirectional threaded rod rotatably passes through a right-side fixing plate, a left end of the bidirectional threaded rod is rotatably connected to a left-side fixing plate, a right end of the bidirectional threaded rod is fixedly connected to a second rotating block, a clamping plate is threadedly connected to the bidirectional threaded rod in the left-right symmetrical manner, an inner side of each of two clamping plates is fixedly connected to a friction pad, a limiting rod is fixedly connected between the two fixing plates, and the limiting rod slidably passes through the two clamping plates.

10. The AR-assisted enhanced fracture reduction fixator according to claim 9, wherein a fixing rod is fixedly connected to the inner wall of the rectangular sleeve in an up-down symmetrical manner, an outer surface of each of two fixing rods is rotatably connected to a guide wheel, and an outer surface of each guide wheel is fixedly connected with a rubber pad.

* * * * *